United States Patent
Klitmose

(10) Patent No.: US 6,620,112 B2
(45) Date of Patent: Sep. 16, 2003

(54) DISPOSABLE LANCET COMBINED WITH A REAGENT CARRYING STRIP AND A SYSTEM FOR EXTRACTING AND ANALYZING BLOOD IN THE BODY UTILIZING SUCH A DISPOSABLE LANCET

(75) Inventor: Lars Peter Klitmose, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/809,735

(22) Filed: Mar. 14, 2001

(65) Prior Publication Data

US 2001/0027277 A1 Oct. 4, 2001

Related U.S. Application Data

(60) Provisional application No. 60/193,926, filed on Mar. 31, 2000.

(30) Foreign Application Priority Data

Mar. 24, 2000 (DK) .......................................... 2000 00495

(51) Int. Cl.⁷ ................................................. A61B 5/00
(52) U.S. Cl. ...................... 600/583; 600/584; 600/365; 606/181; 435/14; 436/169; 422/55
(58) Field of Search ................... 600/573, 575, 600/576, 578, 583, 584, 365, 308, 309, 316, 322, 368; 606/167, 181, 182, 183; 436/68, 95, 169, 164; 604/239, 264, 272–274; 422/56–58, 61, 100, 68.1, 99, 103; 435/4, 14; 204/403.01–403.02

(56) References Cited

U.S. PATENT DOCUMENTS

| | | | |
|---|---|---|---|
| 4,469,110 A | 9/1984 | Slama | 600/583 |
| 4,627,445 A * | 12/1986 | Garcia et al. | 600/583 |
| 4,787,398 A | 11/1988 | Garcia et al. | 600/583 |
| 4,966,159 A | 10/1990 | Maganias | 600/556 |
| 5,231,993 A | 8/1993 | Haber et al. | 600/583 |
| 5,607,401 A * | 3/1997 | Humphrey | 604/239 |
| 5,801,057 A * | 9/1998 | Smart et al. | 436/68 |
| 5,951,492 A | 9/1999 | Douglas et al. | 600/583 |
| 5,971,941 A * | 10/1999 | Simons et al. | 600/573 |
| 6,071,294 A * | 6/2000 | Simons et al. | 606/181 |

FOREIGN PATENT DOCUMENTS

| | | |
|---|---|---|
| DE | 197 05 091 A1 | 2/1999 |
| EP | 0 164 148 A1 | 12/1985 |
| GB | 2 331 935 A | 6/1999 |
| WO | WO 95/24233 | 9/1995 |

* cited by examiner

Primary Examiner—Charles A. Marmor, II
(74) Attorney, Agent, or Firm—Marc A. Began, Esq.; Richard W. Bork, Esq.; Reza Green, Esq.

(57) ABSTRACT

A disposable lancet combined with a reagent carrying strip which carries a reagent that indicates the concentration of a blood component in a blood sample placed in contact with the strip. The reagent carrying strip is connected to the lancet, e.g. by molding. One end of the lancet is sharpened for piercing the skin. The strip is sheet-like and has a first side and a second side, which sides are both accessible for the user, such that the reagent carrying strip can be inserted into a blood glucose meter. A weakened tear line is provided at a connection between the lancet and an edge of the reagent carrying strip so that the reagent carrying strip may be easily disconnected from the lancet.

2 Claims, 4 Drawing Sheets

Figure 1:
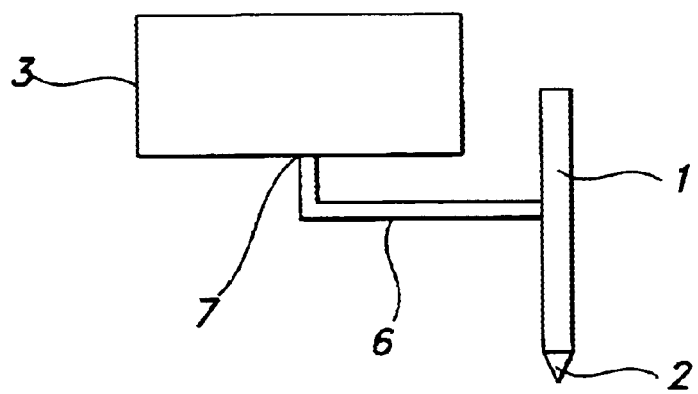

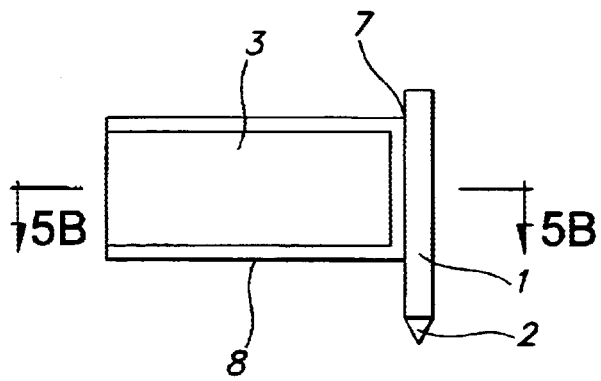
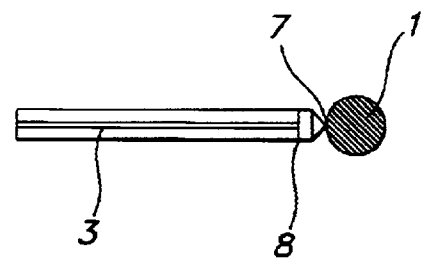
FIG. 5A                FIG. 5B
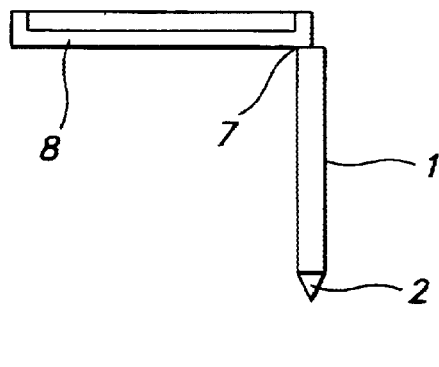
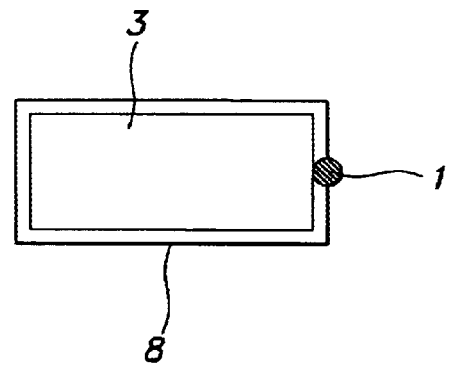
FIG. 6A                FIG. 6B

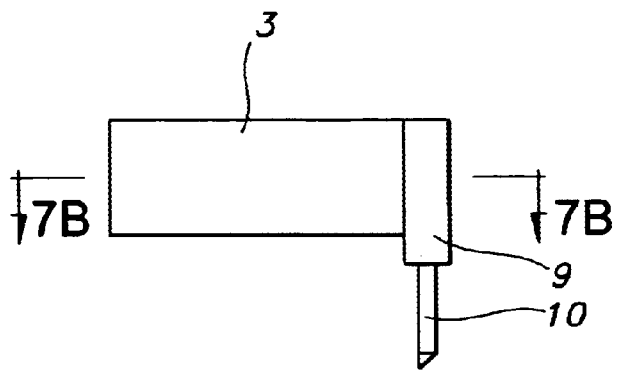
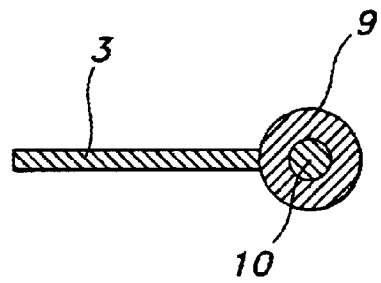
FIG. 7A  FIG. 7B
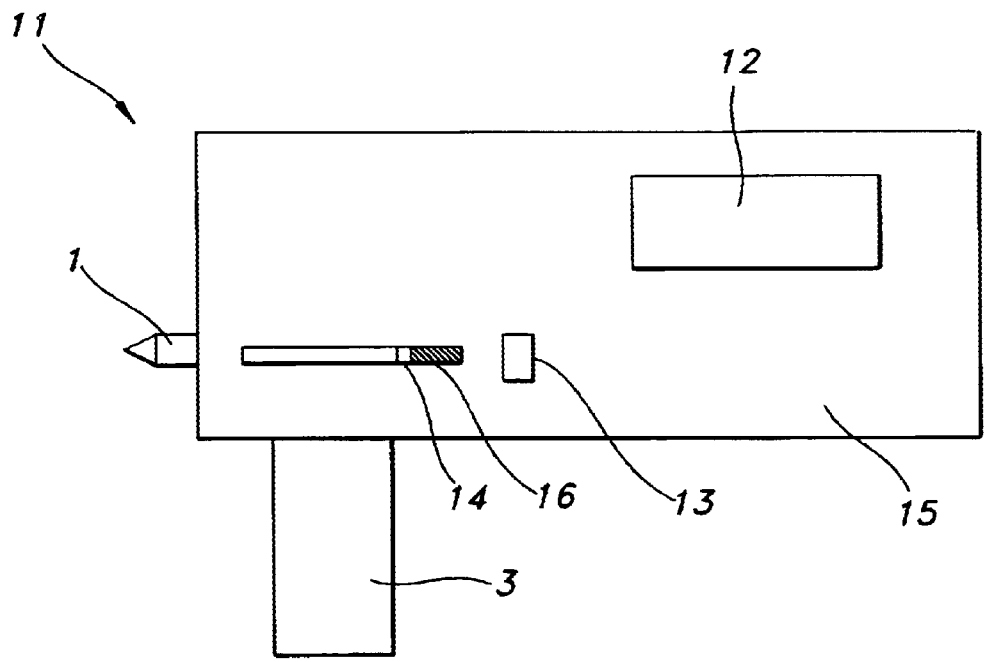
FIG. 8

DISPOSABLE LANCET COMBINED WITH A REAGENT CARRYING STRIP AND A SYSTEM FOR EXTRACTING AND ANALYZING BLOOD IN THE BODY UTILIZING SUCH A DISPOSABLE LANCET

CROSS-REFERENCE TO RELATED APPLICATIONS

This application claims priority under 35 U.S.C. 119 of Danish application no. PA 2000 00495 filed on Mar. 24, 2000 and U.S. provisional application No. 60/193,926 filed on Mar. 31, 2000, the contents of which are fully incorporated herein by reference.

This application claims the benefit U.S. Provisional Application No. 60/193,926 filed Mar. 31, 2000.

The invention relates to a disposable lancet combined with a reagent carrying-strip. The lancet has a sharp distal end for piercing the skin of a user, and a reagent carrying strip, which reacts to a blood sample.

The invention furthermore relates to a system for extracting and analysing blood in a body utilizing a disposable lancet in combination with a reagent carrying strip.

Patients with certain illnesses like diabetes must verify several times a day the sugar content of their blood. This is often done by placing a drop of blood on to a reagent carrying strip, which causes the reactive reagent on the strip to react with the blood. Usually the reagent carrying strip carries an enzyme that reacts with the blood component to be measured. The result of the test is read by a blood g lucose meter before or/and after applying blood. Most such blood glucose meters on the market today either read the change of colour due to the chemical reaction, or read the current produced from the chemical reaction between reagent or blood glucose.

The drop of blood is obtained by piercing the tip of a finger or the earlobe using a portable skin pricker e.g. as known from U.S. Pat. No. 4,469,110. Such a skin pricker comprises a disposable lancet, a lancet holder and a body. The holder is, when armed, worked upon by a spring. When firing the skin pricker, the disposable lancet inserted in the holder is shot forward by the spring. By pressing the tip of the finger against the skin pricker the finger is pierced by the sharp end of the lancet. A drop of blood can then be obtained from the punctured finger and placed onto the reagent carrying strip. After use the lancet is disposed of. When the change in the reagent carried on the strip has been measured, the strip is also disposed of.

Next time a blood sample is required, the patient has to place a new lancet in the holder of the skin pricker and get a hold of a new reagent carrying strip. The reagent carrying strips are often carried in a separate container, which is very inconvenient, since such a separate container is often forgotten or mislaid. Some times the container is integrated with the skin pricker, but since the lancet and the reagent carrying strip are two separate pieces, they are often available in an unequal number. The user therefore often runs out of one of the items first. As a result of this the user must always remember to refill the container with the item needed.

In order to avoid these inconveniences the disposable lancets are sometimes combined with the reagent carrying strip. Such blood-sampling units are known from U.S. Pat. No. 5,231,993 and EP A1 164.148. These known units have a lancet, which is sharpened for piercing the tip of a finger and an integrated reagent carrying strip. They are however not designed to be used in a typical skin pricker of the type described above. The force needed to pierce the finger is delivered by the patient, but for many patients it is psychologically difficult to pierce themselves. Such patients prefer to use an ordinary skin pricker with a disposable lancet. The change of the reagent carrying strip in these known blood-sampling units is unreadable by the standard glucose meters on the market, since these are designed to read an inserted rectangular strip.

It is an object of the invention to provide an ordinary disposable lancet for a skin pricker, which lancet is combined with a reagent carrying strip in order to minimise the amount of loose items a diabetes patient has to carry around. It is also an object to provide a disposable lancet combined with a reagent carrying strip, which strip can easily be read in a standard glucose meter.

This is obtained by a disposable lancet combined with a reagent carrying strip comprising a lancet, with a distal end, which is sharpened for piercing the skin of the user, and a reagent carrying strip, which carries a reagent that indicates the concentration of a blood component in a blood sample placed in contact therewith.

The disposable lancet combination is characterized in that the reagent carrying strip is a sheet-like strip having a first side and a second side, which sides are both accessible for the user, and that the lancet is connected to the reagent carrying strip.

The disposable lancet can be inserted in a skin pricker having the attached reagent carrying strip sliding in a groove in the skin pricker, but the reagent carrying strip could also be disengaged from the lancet before inserting the lancet in the skin pricker. In both ways it is assured that the patient always has a reagent carrying strip available when inserting a new lancet in the skin pricker. After the blood sample has been placed on to the reagent carrying strip, the strip is easily inserted in a standard blood glucose meter.

In one embodiment of the disposable lancet according to the invention the lancet is made from a moldable polymeric material, and the reagent carrying strip is attached to the lancet. Attaching the reagent carrying strip to the lancet can be done by gluing the reagent carrying strip to the lancet. If the reagent carrying strip is made from paper or another fibrous material the strip can be fastened to the disposable lancet without the use of glue simply by folding the strip around the lancet and applying heat and pressure. The surface of the lancet will then start to melt, and connect to the reagent carrying strip.

In another embodiment of the disposable lancet combined with a reagent carrying strip according to the invention the reagent carrying strip is made from a moldable polymeric material, which is moulded around the lancet. Instead of making the strip from a fibrous material as paper, the strip can be made by moulding a moldable polymeric material to a very thin sheet-like strip of film, on to which the reagent material is placed. The lancet can be made by another material, and the reagent carrying strip can be attached to the lancet by moulding it around the lancet.

In another embodiment of the disposable lancet combination according to the invention the reagent carrying strip has a number of edges between the first and the second side, and the lancet is attached to the reagent carrying strip at one of these edges. By applying the disposable lancet onto the reagent carrying strip at one of the edges, disconnecting the two items is made very easy.

In an appropriate embodiment of the disposable lancet according to the invention the lancet is connected to a frame, which frame is attached to the edges of the reagent carrying strip. By framing the reagent carrying strip a stiff construction is possible, which accommodates an easy insertion into the glucose meter.

In yet another embodiment of the disposable lancet combined with a reagent carrying strip according to the invention an arm is connecting the lancet to the reagent carrying strip or to the frame framing the reagent carrying strip. The reagent carrying strip can then be situated a distance from the disposable lancet, but still in connection therewith, forming a combined unit.

In an embodiment of the disposable lancet combined with a reagent carrying strip according to the invention the connecting point between the reagent carrying strip or the frame and the disposable lancet or the arm has a weakened tear line. By this the attached reagent carrying strip can easily be separated from the lancet.

In an embodiment of the disposable lancet combined with a reagent carrying strip according to the invention the reagent carrying strip is rectangular. Most glucose meters present on the market accommodate rectangular reagent carrying strips.

It is also an object of the invention to provide a system for extracting and analysing blood in a body utilizing a disposable lancet combined with a reagent carrying strip, where the disposable lancet is kept in the same position both when obtaining the blood sample and when analysing the blood sample. In the known systems of this kind e.g. as known from WO A 95/24233, especially FIG. 25, the blood-coated strip has to be manually moved from the position where it is coated with blood and to the position where the change in the reagent is being measured. This is very inconvenient for the user.

This is obtained by a system for extracting and analyzing blood in a body utilizing a disposable lancet combined with a reagent carrying strip according to any of the preceding embodiments, which system comprises:

a housing including a spring actuated hammer, into which housing the disposable lancet combined with a reagent carrying strip is placed in a guided position, a button which releases the spring actuated hammer, which then pushes forward the disposable lancet combined with a reagent carrying strip, means for guiding the disposable lancet combination from a retracted position to a deployed position where the tip of the disposable lancet with reagent carrying strip penetrates the skin of the user, a sensor which senses the changes in the reagent placed on said reagent carrying strip, a display for showing a visual readout representing the changes in the reagent which system is characterized in that said sensor is situated in a position in the housing where it can sense the changes in the reagent without manually moving the disposable lancet combined with a reagent carrying strip.

In such a system the disposable lancet combined with a reagent carrying strip just need to be placed in the guided position and fired. There after the user merely has to place a drop of blood onto the reagent carrying strip and to actuate the device, then the change in the reagent is read without removing the disposable lancet combination from the guided position.

The invention will be explained more fully below in connection with a preferred embodiment and with reference to the drawings in which:

FIG. 1 Schematically shows a disposable lancet combination, where the strip is connected through a thin arm.

Figure 2:
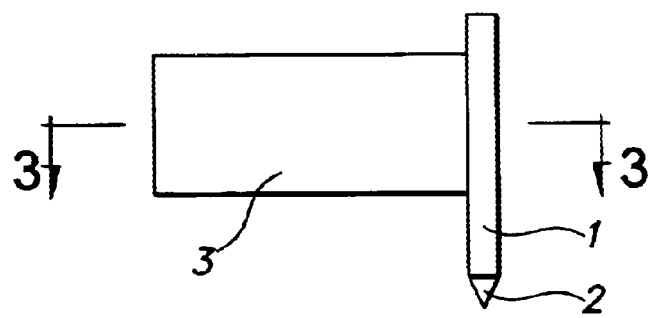

FIG. 2 Schematically shows a disposable lancet combined with a reagent carrying strip, where the strip is connected directly to the lancet.

Figure 3:
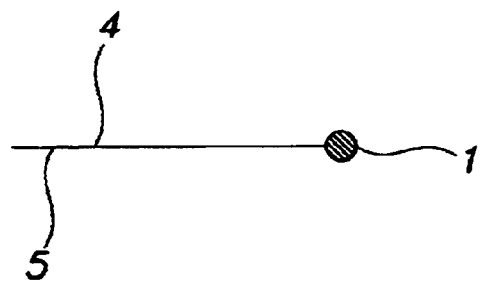
Figure 4A:
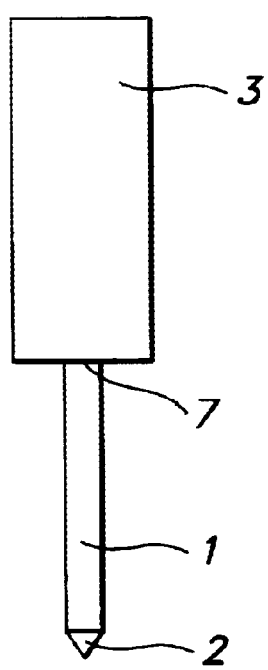
Figure 4B:
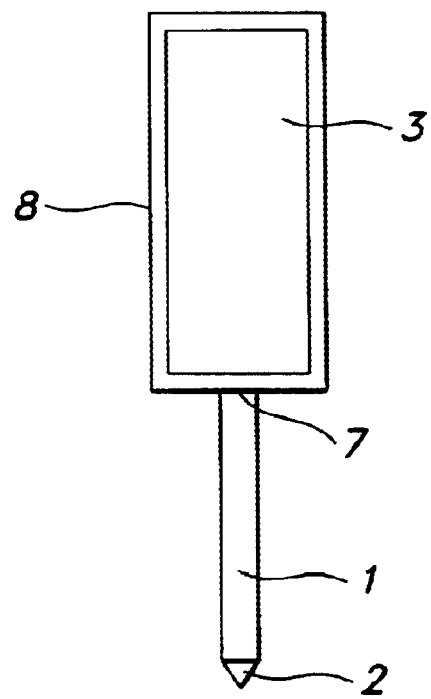
Figure 4C:
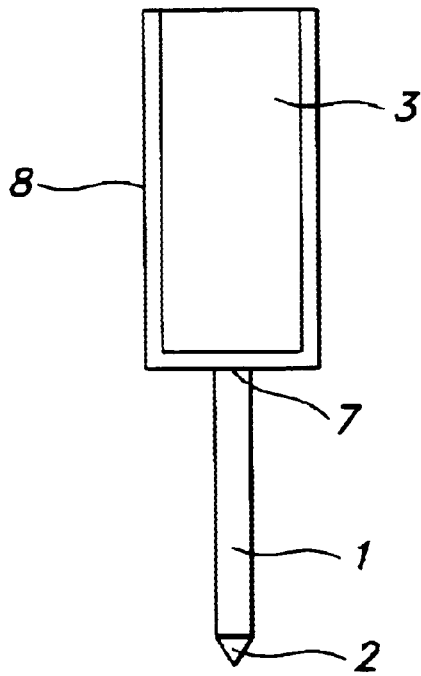
Figure 4D:
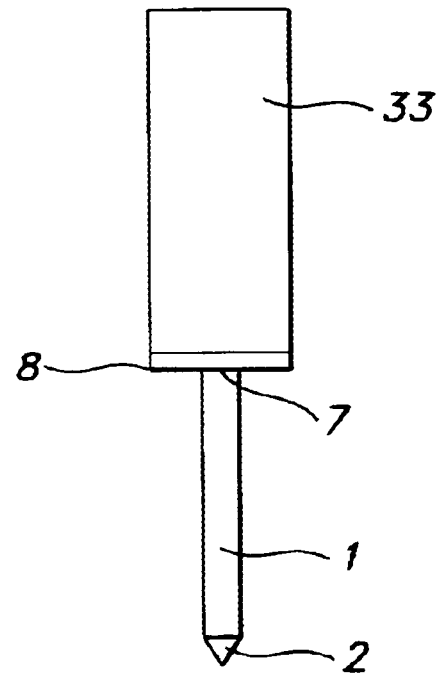

FIG. 3 Shows a sectional view along line AA in FIG. 2.

FIGS. 4A–D Schematically shows a disposable lancet in combination with a reagent carrying strip.

FIG. 5A Schematically shows a disposable lancet combination having a weakened tear-line.

FIG. 5B Shows an expanded sectional view along line AA in FIG. 5A.

FIGS. 6A–B Schematically shows a side-view and a bottom-view of a disposable lancet combined with a reagent carrying strip, where the lancet is attached to one of the sides of the reagent carrying strip.

FIG. 7A Schematically shows a disposable lancet combined with a reagent carrying strip, which strip is moulded around the lancet.

FIG. 7B Shows an expanded view along line AA in FIG. 7A.

FIG. 8 Schematically shows a system for extraction and analysis of blood.

The figures are schematic and simplified for clarity, and they just show details, which are essential to the understanding of the invention, while other details are left out. Throughout, the same reference numerals are used for identical or corresponding parts.

Referring now to the drawing, it can be seen that a disposable lancet 1, 10 combined with a reagent carrying strip 3 according to the invention comprises a lancet 1, 10 with a sharpened distal end 2 for piercing the skin of a patient and a reagent carrying strip 3 connected to the lancet 1, 10.

The reagent carrying strip 3 has two sides 4, 5, both or one of which can carry the reagent that indicates the concentration of glucose in a blood sample. When the reagent carrying strip 3 is placed in contact with a blood sample, the reagent part of the reagent carrying strip 3 perform a chemical reaction resulting in for instance a colour change or a current according to the glucose concentration. This change can then be read by a not shown glucose meter, into which the strip 3 is placed.

The disposable lancet 1, 10 can be connected to the reagent carrying strip 3 through a thin arm 6. As shown in FIG. 1 the connecting point 7 between the arm 6 and the reagent carrying strip 3 is situated at one of the edges of the reagent carrying strip 3. The arm 6 or the disposable lancet 1, 10 could however be connected to one of the two sides 4, 5 of the reagent-carrying strip 3. FIGS. 6A–B shows the disposable lancet 1, 10 being connected directly to the frame at one of the two sides 4, 5.

Both the disposable lancet 1, 10 and the arm 6 can be made of metal, but is preferably made from a mouldable polymeric material. However the material chosen should preferably be a material suitable to be sterilized. In this way the disposable lancets with reagent carrying strip could be sterilized prior to packing the units.

The reagent carrying strip 3 is connected to the lancet 1, 10 preferably through gluing, but can also be applied through melting, as is best shown in FIG. 2 and 3. By folding the reagent carrying strip 3, made from a fibrous material such as paper, around the disposable lancet 1, 10, made from a mouldable polymeric material, and applying heat, the polymeric material will tend to melt on the surface and thereby be locked on to the fibrous reagent carrying strip 3.

As shown in FIGS. 4A–D, the reagent carrying strip 3 can be connected directly to the disposable lancet 1, 10, or the reagent carrying strip 3 can be connected to a frame 8, framing a number of the edges of the reagent carrying strip 3.

The frame 8 can as indicated with a dotted line in FIG. 6A be designed as one unitary frame—somewhat like a well—into which the reagent is placed, without differing from the scope of the claims. If wanted the unitary frame 8 could have a well-like depression on both sides, both carrying a reagent.

When in use the disposable lancet 1, 10 with reagent carrying strip 3 is first inserted into the armed skin pricker. The reagent carrying strip 3 may slide in a groove in the skin pricker. The skin pricker is then fired, and the lancet 1, 10 penetrates the skin of the patient. A drop of blood is disposed on to the attached reagent carrying strip 3, which is then placed in a glucose meter. After the reading of the blood glucose value, the disposable lancet 1, 10 and the attached reagent carrying strip 3 is disposed of.

Before loading the disposable lancet 1, 10 into the skin pricker, the attached reagent carrying strip can be separated from the lancet 1, 10. In order to accommodate such a detachment the connecting point 7 between the reagent carrying strip 3, or the frame 8, and the disposable lancet 1, 10, or the arm 6, can be equipped with a weakened tear-line, which is best seen in FIG. 5B.

The connection 7 between the lancet 1, 10 and the frame 8 need not to run along the entire length of a side of the frame as shown in FIG. 5A. The connection needs only to be at one or at a few points along the side. Instead of a weakened tear-line as shown in figure 5B there could be e.g., two tear-points having the appearance of the tear-line shown in FIG. 5B also when viewed from the side.

As shown in FIGS. 7A–B the reagent carrying strip 3 can be made from a polymeric material which is formed into a very thin film 3. The reagent is applied onto the film 3. The film 3 can be attached to the lancet 1, 10 by moulding the film in a way having a part 9, which surrounds the lancet 1, 10 and is attached to the lancet 1, 10. In this way the disposable lancet 1, 10 with reagent carrying strip 3 can be moulded in one process, by first placing the lancet 1, 10, which is made from metal or from a polymeric material, into the mould and then applying the polymeric material.

In order to avoid the inconveniency of moving the blood-coated strip 3 around the system 11 shown in FIG. 8 uniting a skin pricker and a glucose meter has been developed. The system comprises a housing 15, a hammer 14, a spring 16, a release button 13 and a display 12.

The disposable lancet 1, 10 combined with a reagent carrying strip 3 is placed in a guided position in the housing with the spring 16 in the shown compressed position. Releasing the spring 16 by pressing the release button 13 caused the spring 16 carrying the hammer to move forward. When the hammer 14 impacts the lancet 1, 10 this is also moved forward. The length of the spring 16 is determined so that the tip 2 of the lancet 1, 10 is outside the boundaries of the housing 15 when the spring is released and goes beyond its normal position, but inside the boundaries of the housing 15 when the spring 16 is in its normal position. In this way the finger will be pierced when pressed against the housing 15 upon firing the lancet 1, 10.

After the finger has been pierced a drop of blood can be placed onto the reagent carrying strip 3, which is then automatically guided into the combined skin pricker and glucose meter, where a sensor senses the change in the reagent. In order to place the reagent carrying strip 3 in a readable position the strip 3 can be winded around the lancet 1, 10, or the whole disposable lancet 1, 10 with reagent carrying strip 3 can be automatically shifted to a readable position.

Some preferred embodiments have been shown in the foregoing, but it should be stressed that the invention is not limited to these, but may be embodied in other ways within the subject-matter defined in the following claims. The sheet-like reagent carrying strip could, for example, be formed into a circular tube-shaped element, which is fitted around the lancet without falling outside the scope of the claims.

What is claimed is:

1. A disposable lancet and reagent carrying strip combination comprising:
 a lancet; and
 a reagent carrying strip comprising:
  a sheet having two sides, both of which are accessible to a user and a plurality of edges; and
  wherein the lancet is adjacent to one of the edges and is connected to the reagent carrying strip along an edge at a connection having a weakened tear line.

2. A disposable lancet and reagent carrying strip combination as recited in claim 1, wherein the reagent carrying strip is rectangular.

* * * * *